(12) United States Patent
Walsh et al.

(10) Patent No.: US 10,053,721 B2
(45) Date of Patent: Aug. 21, 2018

(54) ANTIMICROBIAL RESISTANCE STATUS DETERMINATION DEVICE AND METHOD

(71) Applicant: bioMerieux, Inc., Durham, NC (US)

(72) Inventors: John D. Walsh, Bahama, NC (US); Christopher S. Ronsick, Durham, NC (US); Jones M. Hyman, Wake Forest, NC (US); Mark S. Wilson, Hillsborough, NC (US)

(73) Assignee: bioMerieux, Inc., Durham, NC (US)

( * ) Notice: Subject to any disclaimer, the term of this patent is extended or adjusted under 35 U.S.C. 154(b) by 0 days.

(21) Appl. No.: 15/166,768

(22) Filed: May 27, 2016

(65) Prior Publication Data

US 2016/0349178 A1    Dec. 1, 2016

Related U.S. Application Data

(60) Provisional application No. 62/168,271, filed on May 29, 2015.

(51) Int. Cl.
| | |
|---|---|
| *C12M 1/02* | (2006.01) |
| *C12Q 1/04* | (2006.01) |
| *G01N 21/27* | (2006.01) |
| *G01N 21/51* | (2006.01) |

(52) U.S. Cl.
CPC ............ *C12Q 1/04* (2013.01); *G01N 21/272* (2013.01); *G01N 21/51* (2013.01)

(58) Field of Classification Search
CPC ....................................................... C12M 1/02
See application file for complete search history.

(56) References Cited

U.S. PATENT DOCUMENTS

| | | | | | |
|---|---|---|---|---|---|
| 5,164,796 | A | * | 11/1992 | Di Guiseppi | .......... C12M 41/36 356/445 |
| 2010/0273208 | A1 | * | 10/2010 | Takenaka | ............... C12M 41/36 435/34 |

* cited by examiner

*Primary Examiner* — Rosanne Kosson

(57) ABSTRACT

A device and method for determining antimicrobial resistance status of a microorganism from a positive sample bottle is provided. The device may include a housing having a chamber for receiving a vial containing a sample; a light source positioned to direct light through a side of the chamber; and a photodetector positioned such that light transmitted or scattered by the sample is sensed by the photodetector. The device may also include a heat source and/or an agitation device. The method includes providing the device, loading a sample from an automated sample culture system into the vial; interrogating the vial using the light source and the photodetector; and determining the antimicrobial resistance status of the microorganism in the sample based on the interrogating step. The method may also include heating and/or agitating the sample.

26 Claims, 8 Drawing Sheets

ANTIMICROBIAL RESISTANCE STATUS DETERMINATION DEVICE AND METHOD

RELATED APPLICATION INFORMATION

This application claims the benefit of U.S. Provisional Patent Application Ser. No. 62/168,271, filed May 29, 2015, the disclosure of which is incorporated herein by reference in its entirety.

FIELD OF THE INVENTION

The present application is directed to a device, system, and method for determining the antimicrobial resistance status of microorganisms. The system may be incorporated into an automated instrument for quickly determining the antimicrobial resistance status of microorganisms cultured in a sample bottle and then transferred to the device.

BACKGROUND

Bottles for culturing of blood for the presence of microorganism and related instruments for analyzing such bottles in a noninvasive manner are known in the art and described in the patent literature. See U.S. Pat. Nos. 5,858,769; 5,795,773; 4,945,060; 5,094,955; 5,164,796; 5,217,876; and 5,856,175. The bottles and instruments of the above-listed patents have been commercialized with success by the present assignee under the trademark BacT/ALERT.

The bottles described in these blood culture instruments utilize colorimetric sensors placed in the bottom of the bottle and in contact with the sample media to determine the presence/absence of bacterial growth. Once a clinical/industry sample is added to the liquid growth media present in the bottle and incubation occurs, the concentration of carbon dioxide increases as the number of microorganisms increase; carbon dioxide is a respiration by-product of bacterial growth. Alternatively, changes to the media pH that are related to the growth of microorganisms can also be monitored by the sensor. The basic operation of the BacT/ALERT sensor and monitoring electronics is described in U.S. Pat. No. 4,945,060 and also in an article by Thorpe et al. in "BacT/Alert: an Automated Colorimetric Microbial Detection System," which was published in the Journal of Clinical Microbiology, July 1990, pp. 1608-12. The '060 patent and the Thorpe et al. article are incorporated by reference here.

While the BacT/ALERT sensing system is robust and has been used in blood culture systems successfully for many years, it does have a few areas for improvement. For example, the BacT/ALERT system identifies a positive culture but does not provide information on whether the microorganism in the culture is resistant to antimicrobial treatment. Further, the BacT/ALERT system was not designed to facilitate immediate processing of a positive bottle, and the cumulative time required to manually remove a positive bottle and subculture its contents to prepare a log phase microbial suspension for testing significantly delays identification of the antimicrobial resistance status of the sample. However, a new blood culture system soon to be launched commercially has capability to automatically unload a positive bottle and transfer it to an adjacent instrument for processing. Microbial cells, already in logarithmic growth phase at time of detection by the continuously monitoring culture system, may be immediately and automatically transferred to the device of this invention under controlled conditions that greatly minimize any lag phase in growth of the subculture.

There is a long-felt but unmet clinical need to have a device and method for identifying antimicrobial resistance in a microorganism directly from a positive blood culture bottle within a few hours of detection. The device of the current invention has the capability to meet this need by minimizing any manipulation-induced lag in microbial growth upon subculture through timely, controlled and automated processing of a positive bottle, and by continuously monitoring the optical density of said subcultures.

SUMMARY

A device and method for automatic detection of antimicrobial resistance in microorganisms present in a positive blood culture bottle is disclosed. In a first aspect, a device for determining antimicrobial resistance status of a microorganism from a positive sample bottle is provided. In some embodiments, the device includes a housing having at least one chamber for receiving a vial containing a sample; a light source positioned to direct light through a side of the chamber; and a photodetector positioned such that light transmitted or scattered by the sample is sensed by the photodetector.

In some embodiments, the light source is an LED electronically connected to a first printed circuit board. In an embodiment, the photodetector is a photodiode electronically connected to a second printed circuit board. For example, the photodetector may be positioned at an angle from the light source selected from the group consisting of 90° and 180°. In some embodiment, the device includes a heat source thermally connected to the housing. In one embodiment, the heat source is configured to maintain a temperature of the chamber at between about 20° C. and about 45° C. In further embodiments, the device includes an agitation device operably connected to the housing and configured to agitate the housing. For example, the agitation device may be a step motor configured to rock the housing at least +/−18° from horizontal. In some embodiments, the agitation device continuously agitates the housing as the photodetector senses light to generate real-time measurements of optical density of the sample.

In some embodiments, the device further includes a vial containing sterile culture media and an antimicrobial agent. In further embodiments, the device is part of a system and also includes a transfer mechanism and mechanical arm configured to transport the sample from an automated sample culture system to the vial.

In a second aspect, another device for determining antimicrobial resistance status of a microorganism from a positive sample bottle is provided. In some embodiments, the device includes a housing having at least one chamber for receiving a sample; an LED electronically connected to a first printed circuit board and positioned to direct light through a side of the chamber; a photodiode electronically connected to a second printed circuit board and positioned such that light transmitted or scattered by the sample is sensed by the photodiode; a rubber heater adhered to the side of the housing and configured to maintain a temperature of the at least one chamber at between about 20° C. and about 45° C.; and a step motor configured to rock the housing at least +/−18° from horizontal.

In a third aspect, a method for determining antimicrobial resistance status of a microorganism from a positive blood culture bottle is provided. In some embodiments, the method includes providing a device comprising a housing having at least one chamber for receiving a vial containing sterile culture media and an antimicrobial agent in the chamber, a light source positioned to direct light through a side of the chamber; and a photodetector positioned opposite the LED such that light transmitted or scattered by the sample is sensed by the photodetector; loading a sample from an automated sample culture system into the vial; interrogating the vial using the light source and the photodetector; and determining the antimicrobial resistance status of the microorganism in the sample based on the interrogating step.

In some embodiments, the light source is an LED electronically connected to a first printed circuit board. In further embodiments, the photodetector is a photodiode electronically connected to a second printed circuit board. In one embodiment, the method includes heating the positive sample bottle in the chamber. In an embodiment, the heating maintains the positive sample bottle at between about 20° C. and about 45° C. In further embodiments, the method includes agitating the housing using a step motor. For example, the agitating may rock the housing at least +/−18° from horizontal. In an embodiment, the method includes continuously agitating the housing while interrogating the vial to generate real-time measurements of optical density of the sample.

In an embodiment, the method includes transporting the sample from the automated sample culture system to the vial using a transfer mechanism and mechanical arm. In some embodiments, the method includes measuring a change in an optical density of the sample over time. In an embodiment, the method includes determining a growth curve for the microorganism based on the change in the optical density of the sample over time. In further embodiments, the method includes determining a slope of the growth curve and determining that the microorganism is resistant to the test antimicrobial based on analysis of a change in the slope of the growth curve at any time during the culture period. For example, an increase in the slope of the growth curve about a predetermined or minimum amount may indicate that the microorganism is growing at the concentration of antimicrobial agent in the vial and therefore indicate that the microorganism is resistant. Conversely, the method includes determining that the microorganism is sensitive to the test antimicrobial when the slope of the growth curve is decreasing or flat throughout the culture period, or less than a predetermined amount.

In still further embodiments, the device further includes a control vial having no antimicrobial agent, and the method includes placing a control sample from the automated sample culture system into the control vial, wherein the sample and the control sample are from the positive sample bottle; interrogating the control vial using the LED and the photodiode; determining a change in an optical density of the control sample over time; and comparing the change in the optical density of the sample over time to the change in the optical density of the control sample over time. In an embodiment, the method includes determining a growth curve for the microorganism based on the change in the optical density of the sample over time; and determining a slope of the growth curve. In some embodiments, the method includes determining that the microorganism is sensitive to the test antimicrobial agent when the slope of the sample growth curve is decreasing or flat throughout the culture period, and the slope of the control sample growth curve increases at any time during the culture period. In a similar embodiment, the method includes determining that the microorganism is resistant to the test antimicrobial agent when the slopes of both sample and control sample growth curves increase at any time during the culture period.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

The antimicrobial resistance device and method of this disclosure will be described in conjunction with the appended drawings, in which.

DETAILED DESCRIPTION

Figure 1:
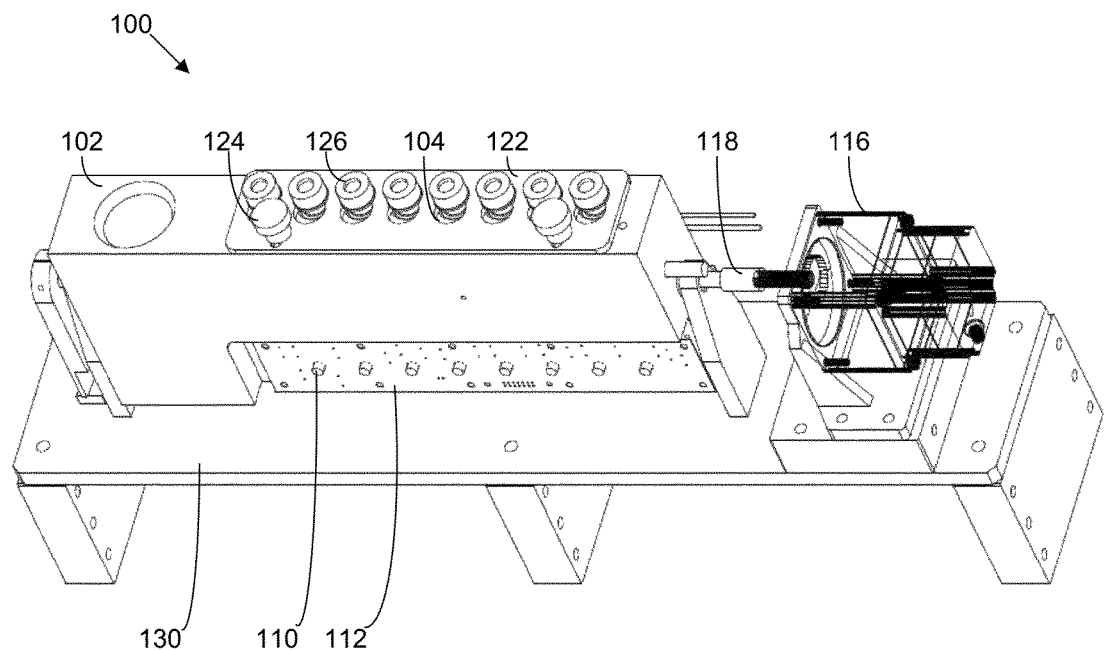
FIG. 1 is a perspective view of a device for determining antimicrobial resistance status of a microorganism from a positive sample bottle, in accordance with an embodiment of the present disclosure.

The present invention will now be described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain embodiment, features or operation of one embodiment can apply to others.

In the drawings, the thickness of lines, layers, features, components and/or regions may be exaggerated for clarity. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. While the term "comprising" may be used herein, it should be understood that the objects referred to as "comprising" elements may also "consist of" or "consist essentially of" the elements. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "automatically" means that the operation can be substantially, and typically entirely, carried out without human or manual input, and is typically programmatically directed or carried out. The term "electronically" includes both wireless and wired connections between components. The term "about" means that the recited parameter or value can vary by between about +/−20%.

Figure 2:
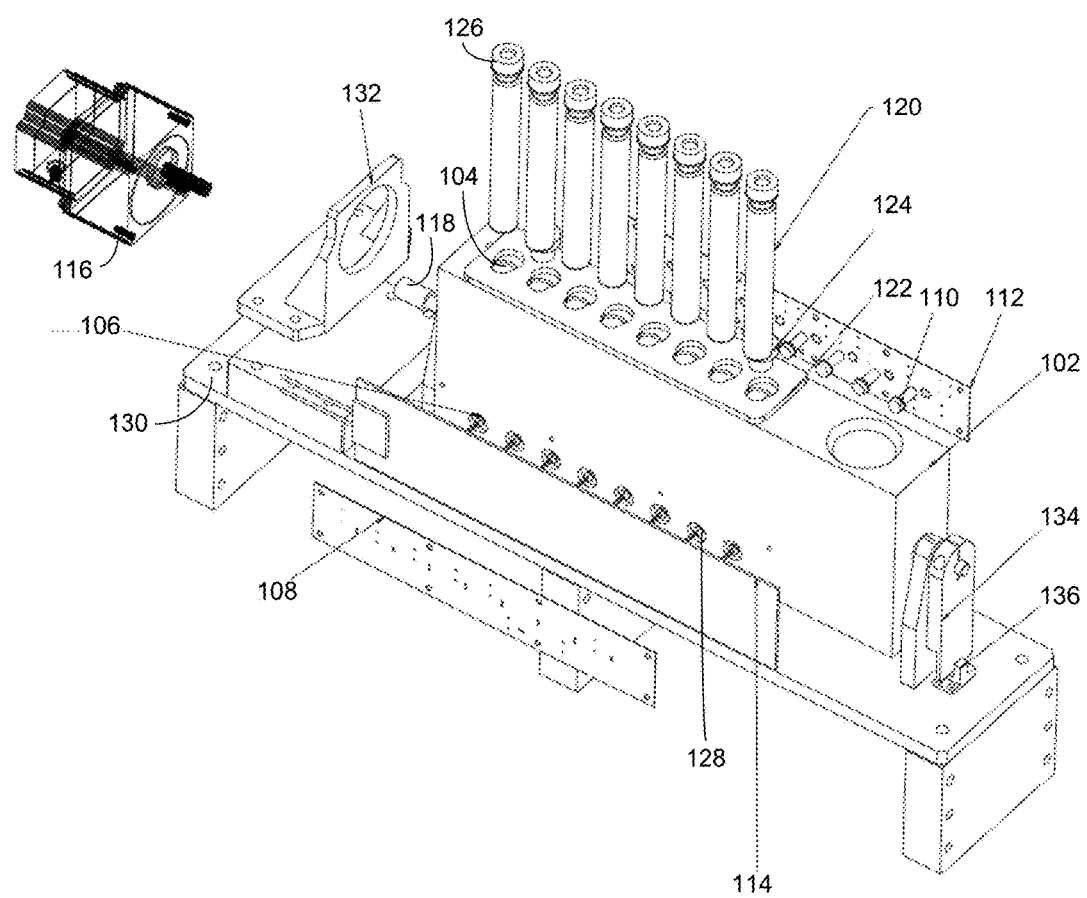
FIG. 2 is an exploded view of a device for determining antimicrobial resistance status of a microorganism from a positive sample bottle, in accordance with an embodiment of the present disclosure.
Figure 3:
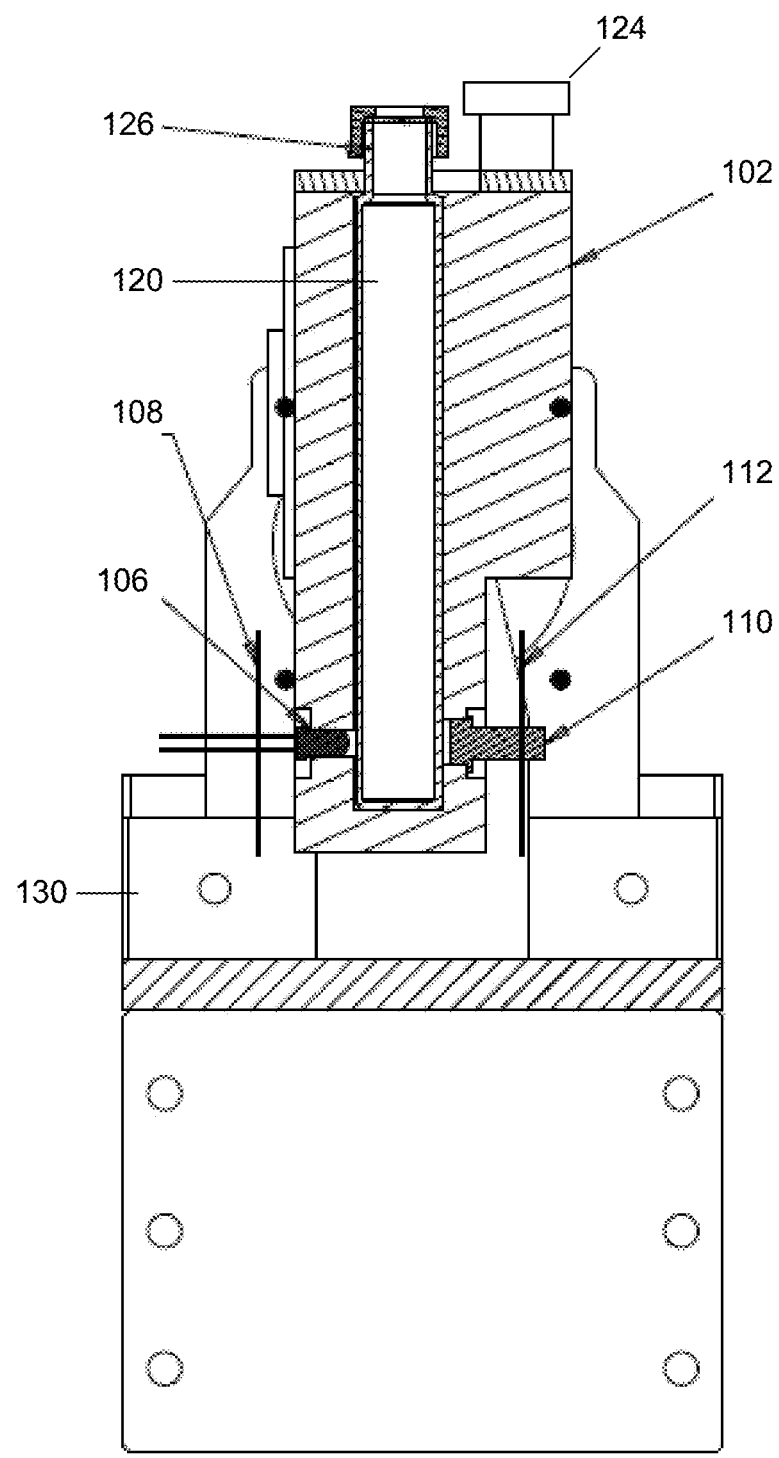
FIG. 3 is a sectional view of a device for determining antimicrobial resistance status of a microorganism from a positive sample bottle, in accordance with an embodiment of the present disclosure.

Turning now to FIGS. 1-3, a device 100 for determining antimicrobial resistance status of a microorganism from a positive sample bottle is provided. In some embodiments, the device includes a housing 102 comprising at least one chamber 104 for receiving a vial containing a sample; a light source positioned to direct light through a side of the chamber; and a photodetector positioned such that light transmitted or scattered by the sample is sensed by the photodetector. In some embodiments, the device also includes a heat source 114 thermally connected to the housing 102 and/or an agitation device 116 configured to agitate the housing 102.

In one embodiment, the light source is a light emitting diode (LED) 106. In further embodiments, the light source may be selected from any number of suitable light sources. For example, light sources capable of emission in the ultraviolet, visible and near-infrared portions of the electromagnetic spectrum may be utilized and are known to those skilled in the art. Alternatively, narrowband light sources, such as light emitting diodes or lasers, may be used. For example, light emitting diodes are available from 240 nm to in excess of 900 nm and the sources have a spectral bandwidth of 20-40 nm (full width at half maximum). Lasers are available in discrete wavelengths from the ultraviolet to the near-infrared.

In one embodiment, the photodetector is a photodiode 110. In further embodiments, the photodetector is a photomultiplier tube, charge coupled device (CCD) detector array, or electron multiplying charge coupled device (EMCCD) detector array. Other types of detection units may be used.

As used herein, antimicrobial resistance status means whether a microorganism is resistant to an antimicrobial compared to a wild-type or sensitive stain of the same species of microorganism. In some embodiments, antimicrobial resistance indicates that the resistant microorganism has a faster growth rate in the presence of the antimicrobial than the wild-type microorganism. In some embodiments, a determination that the microorganism is resistant to a given concentration of an antimicrobial is one outcome of a screening assay. For example, a microorganism can be determined to be resistant or sensitive. In this example, resistant means that the microorganism is capable of growing in a specific concentration of the antimicrobial agent. In contrast, a sensitive microorganism is not capable of growing in the specific concentration of the antimicrobial agent. In an embodiment, the antimicrobial resistance status of the microorganism will affect treatment strategies for treating the patient. For example, a patient that has been found to have a methicillin-resistant infection will be treated differently from a patient found to have a methicillin-sensitive infection. As shown herein, in some embodiments the device and method of the present disclosure is capable of determining the antimicrobial resistance status of a microorganism within 30 minutes, 1 hour, 1.5 hours, 2 hours, 2.5 hours, 3 hours, 3.5 hours, 4 hours, 4.5 hours, 5 hours, 5.5 hours, or 6 hours.

There are a variety of mechanisms that can provide antimicrobial resistance to a microorganism. For example, a microorganism may have inherent resistance to an antimicrobial agent. The inherent resistance may be due to a basal level of gene expression or an induced level of gene expression (e.g., higher or lower than a basal level). In some embodiments, the induced level of gene expression is a result of growing in the presence of the antimicrobial agent. In further embodiments, antimicrobial resistance may be a result of horizontal gene transfer within or between populations of microorganisms. In some embodiments, resistance may be a result of a heterogeneous population that comprises resistant and sensitive microorganisms.

The device is configured to determine whether a microorganism is resistant to an antimicrobial by evaluating the optical density or absorbance of the sample in the vial over time. As used herein, "optical density" means the measure of the amount of light absorbed by a suspension of bacterial cells or a solution of an organic molecule for a given wavelength. As the population of microorganisms in the suspension increases, the amount of light absorbed by the suspension increases. A growth curve for the microorganism can be determined from the optical density measurements and a slope of the growth curve can be evaluated to determine whether the microorganism is increasing in population, decreasing in population, or remaining the same.

In one embodiment, the microorganism is a gram positive or gram negative bacteria. For example, the microorganism may be a gram negative bacteria such as *C. freundii, E. aerogenes, E. cloacae, E. coli, K. oxytoca, K. pneumoniae, M. morganii, P. mirabilis, P. stuartii, P. vulgaris, S. enteritidis, S. marcescens, A. baumanii, N. minigitidis, H. influenza, P. aeruginosa, B. cepacia* or *S. maltophilia*. In other examples, the microorganism may be a gram positive bacteria such as *E. faecalis, E. faecium, L. monocytogenes, S. aureus, S. capitis, S. epidermidis, S. hominis, S. lugdunensis, S. warneri, S. agalactiae, S. bovis, S. mitis, S. oralis, S. pneumoniae*, or *S. pyogenes*. In some embodiments, the microorganism is a fungi or yeast, such as *C. albicans, C. glabrata, C. krusei, C. parasilosis*, or *C. tropicalis*.

In one embodiment, a specimen (e.g., blood or tissue) is taken from a patient and cultured in an automated sample culture system (not shown). The BacT/ALERT system is one such system. Within the automated sample culture system, the specimen is cultured in a sample bottle. When the sample bottle is determined to be positive for microorganism growth, a sample may be extracted from the positive sample bottle and transported to the device 100 for determining antimicrobial resistance status.

In some embodiments, the device includes a housing 102 that defines at least one chamber 104 for receiving a sample. For example, the housing 102 may be an aluminum block having one or more chambers 104 configured to hold glass or clear plastic assay tubes. In an embodiment, the housing 102 is constructed of a thermally conductive material, such as a metal. In some embodiments, the housing 102 includes a pivot mount 118 on at least one end such that the housing 102 can pivot along a horizontal axis.

In an exemplary embodiment, the housing 102 defines one or more chambers 104 for receiving the sample from the automated sample culture system. For example, the chamber 104 may be shaped to receive a vial 120. In some embodiments, the chamber 104 is sized such that the vial 120 fits in the chamber 104 without significant room for vial movement within the chamber 104 when the housing 102 is agitated. In further embodiments, the chamber 104 includes a resilient surface (not shown) to reduce movement of the vial 120 within the chamber 104 when the housing 102 is agitated. For example, the chamber 104 may include a cushion that securely holds the vial 120 in the chamber 104 when the housing 102 is agitated. In some embodiments, the housing 102 includes a collar 122 to hold the vial 120 or vials in the chambers 104 after being loaded into the housing 102. For example, the collar 122 may be movable between a first position that permits loading of the vial 120 into the chamber 104 and a second position that prevents unloading of the vial 120 from the chamber 104. The collar 122 may be lockable into the first and/or second position. For example, the collar may interact with a threaded knob 124 that can lock the collar 122 into position.

In some embodiments, the vial 120 is a transparent assay tube. For example, the vial 120 may be made of glass or clear polymer such that the light from the LED can pass through the sides of the vial. In an embodiment, the vial includes a cap 126 that prevents fluid in the vial 120 from escaping when the housing 102 and/or vial 120 are agitated. In some embodiments, the cap 126 includes a pierceable septum that can be pierced with a needle to inject sample and then reseals when the needle is withdrawn. In this manner, the sample can be withdrawn from the positive sample bottle (not shown), transported to the housing 102, and injected into the vial 120 without exposing workers to potentially infectious microorganisms. The vial 120 is designed to contain the sample during agitation and permit interrogation of the sample through the transparent sides.

In an embodiment, the vial 120 includes a preloaded antimicrobial. For example, the vial may include a cephalosporin (e.g., cefoxitin), glycopeptide (e.g., vancomycin), fluoroquinalone (e.g., ciprofloxacin) or carbapenem (e.g., imipenem) antimicrobial. Combinations of other cephalosporin antibiotics may be used to measure extended spectrum beta lactamase (ESBL) activity (e.g., cefotaxime, ceftazidime, cefepime). The vial may also include certain specific inhibitors such as EDTA, clavulanic acid, cloxacillin or phenyl boronic acid. In one embodiment, the inhibitor may be used to determine the mechanism of antimicrobial resistance. For example, antimicrobial resistance as a result of an enzyme may be determined by providing a test vial comprising the antimicrobial and an inhibitor of the enzyme and comparing the growth curve to a control vial that includes the antimicrobial but does not include the inhibitor. In some embodiments, the vial 120 includes a known amount or concentration of the antimicrobial. In some embodiments, a paired set of vials are provided and one of the paired set includes the antimicrobial while a second of the paired set does not include the antimicrobial. A variety of antimicrobials may be tested using the device and method disclosed herein. Similarly, antifungal solutions may also be tested to identify resistant fungal infections in one embodiment. In some embodiments, the vial 120 is loaded with antimicrobial after the vial 120 is placed into the chamber 104, e.g., prior to the sample being placed in the vial, concurrently with the sample being placed in the vial, or after the sample is placed in the vial.

As discussed, the sample is cultured in a sample bottle and is transported to the vial 120. In an embodiment, the sample is a blood sample. In some embodiments, the sample may be a clinical or non-clinical sample suspected of containing one or more microbial agents. Clinical samples include, but are not limited to, blood, serum, plasma, blood fractions, joint fluid, urine, semen, saliva, feces, cerebrospinal fluid, gastric contents, vaginal secretions, tissue homogenates, bone marrow aspirates, bone homogenates, sputum, aspirates, swabs and swab rinsates, other body fluids, and the like. Non-clinical samples that may also be tested and include, but are not limited to, foodstuffs, beverages, pharmaceuticals, cosmetics, water (e.g., drinking water, non-potable water, and waste water), seawater ballasts, air, soil, sewage, plant material (e.g., seeds, leaves, stems, roots, flowers, fruit), blood products (e.g., platelets, serum, plasma, white blood cell fractions, etc.), donor organ or tissue samples, biowarfare samples, and the like.

In FIG. 2, the LED 106, photodiode 110, and first and second printed circuit boards 108, 112 are disclosed, in accordance with an embodiment of this disclosure. The LED 106 is positioned in an opening 128 in the housing 102 that allows the LED 106 to direct light into the chamber 104 and through the walls of the vial 120. In an embodiment, the LED 106 is positioned in the housing 102 such that the LED 106 directs light through a lower portion of the vial 120.

In an embodiment, the LED 106 emits light at a predetermined wavelength. For example, the LED 106 may emit light at 660 nm. In some embodiments, the wavelength of light is selected such that microorganisms of interest absorb the light in a strongly population density dependent manner.

In some embodiments, the LED 106 is connected to the first printed circuit board 108. In an embodiment, the first printed circuit board 108 controls the activation of the LED 106 and is electronically connected to a computing device processor (not shown). For example, the computing device processor may specify the frequency of activation of the LED 106.

The photodiode 110 is a semiconductor diode that generates a potential difference or changes its electrical resistance when exposed to light, in accordance with an embodiment of this disclosure. In some embodiments, the photodetector is positioned opposite the light source in the housing 102 such that the light from the light source 106 passes through the chamber 104 and the vial 120 and is sensed by the photodetector. In other words, the photodetector may be positioned at a 180° angle from the light source. In this manner, some of the light emitted from the light source is absorbed by the sample in the vial 120 and this absorption is sensed by the photodetector. In further embodiments, the photodetector is positioned at a different angle relative to the light source. For example, the photodetector may be positioned at a 90° angle relative to the light source. In this way, nephelometry-like illumination causes light from the light source to illuminate the sample but the light does not pass directly into the photodiode. In this embodiment, the photodetector only detects light scattered from the components of the sample. This arrangement of photodetector and light source may increase sensitivity with certain types of samples.

In an embodiment, the photodiode 110 is connected to the second printed circuit board 112 to monitor the change in light being sensed by the photodiode 110. The second printed circuit board 112 may be connected to a computing device processor (not shown), which can calculate the absorbance based on the light emitted from the LED 106 and the light received by the photodiode 110. In some embodiments, the computing device processor determines the growth rate of the microorganism in the sample based on the optical density of the solution or change in optical density over time (e.g., change in slope). In some embodiments, analysis of the growth rate of the microorganism in the presence and/or absence of antimicrobials can be used to determine the antimicrobial resistance status of the microorganism.

In some embodiments, the device 100 further includes a heat source 114. For example, the device 100 may include a heater connected to the side of the housing 102. In an embodiment, the heat source 114 is a rubber heater adhered to the side of the housing 102 such that the chambers 104 are maintained at a consistent temperature. In one embodiment, the heat source 114 is configured to maintain the temperature of the chamber at about +/−35° C. to about +/−37° C. For example, the temperature of the chamber may be maintained at about +/−36° C. In another embodiment, the heat source 114 is configured to maintain the temperature of the chamber 104 at a predetermined temperature set by the user. For example, the user may modify the set temperature of the device to accommodate specific types of microorganisms or to encourage faster or slower microorganism growth (e.g. 34° C. for MRSA assays, 20-25° C. for sterility testing for fungi, or about 45° C. for the growth of thermophilic spoilage microorganisms). In some embodiments, the heat source 114 is capable of separately maintaining the temperature of two or more chambers. For example, one chamber may be maintained at a first predetermined temperature and a second chamber may be maintained at a second predetermined temperature. In another example, the upper and lower temperature set point for each chamber may be set by the user, e.g., may be set at 15° C., 20° C., 25° C., 30° C., 35° C., 40° C., 45° C., 50° C., 55° C., or 60° C. In one embodiment, the heat source 114 is controlled by the computing device processor.

In a further embodiment, the device 100 includes an agitation device 116 for agitating the housing 102. In one embodiment, the agitation device 116 is a step motor functionally engaging the housing 102 and configured to rock the housing 102 along a horizontal axis. For example, the step motor may be positioned on a base 130 adjacent the housing 102 and engaging the pivot mount 118 to rock the housing 102 along the horizontal axis. In some embodiments, an agitation device bracket 132 is mounted on the base 130 and maintains the orientation of the agitation device 116 as the housing 102 is rocked. In one embodiment, the agitation device 116 rocks the housing such that the sample, antimicrobial, and broth in the vial is aerated and mixed.

In some embodiments, the agitation device 116 rocks the housing 102 at a predetermined frequency or degree. In some embodiments, the user selects the frequency, duration, and degree of agitation. For example, the user may determine that the agitation device 116 rocks the housing +/−18 degrees from horizontal at 36 cycles/min for 30 seconds. It should be understood that larger degrees of rocking may also be used. For example, the agitation device 116 may rock the housing 102 at least +/−135 degrees, +/−125 degrees, +/−115 degrees, +/−105 degrees, +/−90 degrees, +/−75 degrees, +/−60 degrees, +/−45 degrees, +/−30 degrees, +/−25 degrees, +/−20 degrees, +/−15 degrees, +/−10 degrees, or +/−5 degrees from horizontal. In some embodiments, the angle of agitation may be related to the size of the vial. For example, it may be beneficial to use a larger angle of agitation for larger vials to ensure adequate mixing of the sample in the vial. Further, the agitation device 116 may change the duration and/or frequency of rocking as well. For example, the agitation device may rock the housing at 10 cycles/min, 20 cycles/min, 25 cycles/min, 30 cycles/min, 40 cycles/min, 50 cycles/min, 60 cycles/min, 80 cycles/min, or 100 cycles/min to increase or decrease mixing and agitation in the vial. Similarly, the agitation device 116 may agitate the vial for 5 seconds, 10 seconds, 15 seconds, 20 seconds, 25 seconds, 35 seconds, 40 seconds, 45 seconds, 1 minute, 2 minutes, 5 minutes, or longer.

In one embodiment, the agitation device continuously agitates that housing as the light source and photodetector take readings of the sample in the vial. For example, the light source may continuously illuminate the same. Similarly, the photodetector may take a reading every 5 seconds, every 2 seconds, every 1 second, every 0.5 second, or at another interval during agitation to capture moment-to-moment changes in the optical density of the sample. These increased reading frequencies assist in reducing error in the measurement. This embodiment, eliminates the step of halting the rocker before taking a reading.

It should be understood that in some embodiments the frequency of reading will relate to the size of the vial, the amount of fluid in the vial, and/or the angle of agitation. For example, the fluid in the vial rocks in the housing during agitation. As the fluid rocks in the vial, it slides up and down the side of the vial. Depending on the position of the photodetector, the fluid may intermittently pass out of range for a reading. In one example, multiple photodetectors (e.g., a photodetector positioned to take a reading near the top of the vial and a second photodetector positioned to take a reading near the bottom of the vial) may be used. Dual optics, such as in this example, may further increase the frequency to 0.5 seconds or less as the fluid in the vial does not pass out of range of at least one of the photodetectors at any point during agitation.

In some embodiments, the agitation device 116 is configured to halt for a period of time to allow an optical density or absorption measurement to be taken. For example, the agitation device 116 may halt every 30 second for 15 seconds to allow settling and/or foaming to decrease and then an optical density measurement is taken before the agitation device 116 resumes rocking the housing 102. In an embodiment, the agitation device 116 is controlled by the computing device processor. In an embodiment, the agitation device 116 further comprises a position flag 134 used to determine the orientation of the housing 102 and/or a photoelectric home sensor 136 used to determine the default or home position of the housing.

Turning briefly to FIG. 3, a sectional view of a device for determining antimicrobial resistance status of a microorganism from a positive sample bottle is provided, in accordance with an embodiment of the present disclosure. The sectional view presents a cross section of the device 100 including the vial 120 in the chamber 104, the housing 102, the LED 106, the photodiode 110, and the first PCB 108 and the second PCB 112, mounted on the base 130. The knob 124 that may secure the collar 122 in place is also provided.

Figure 4:
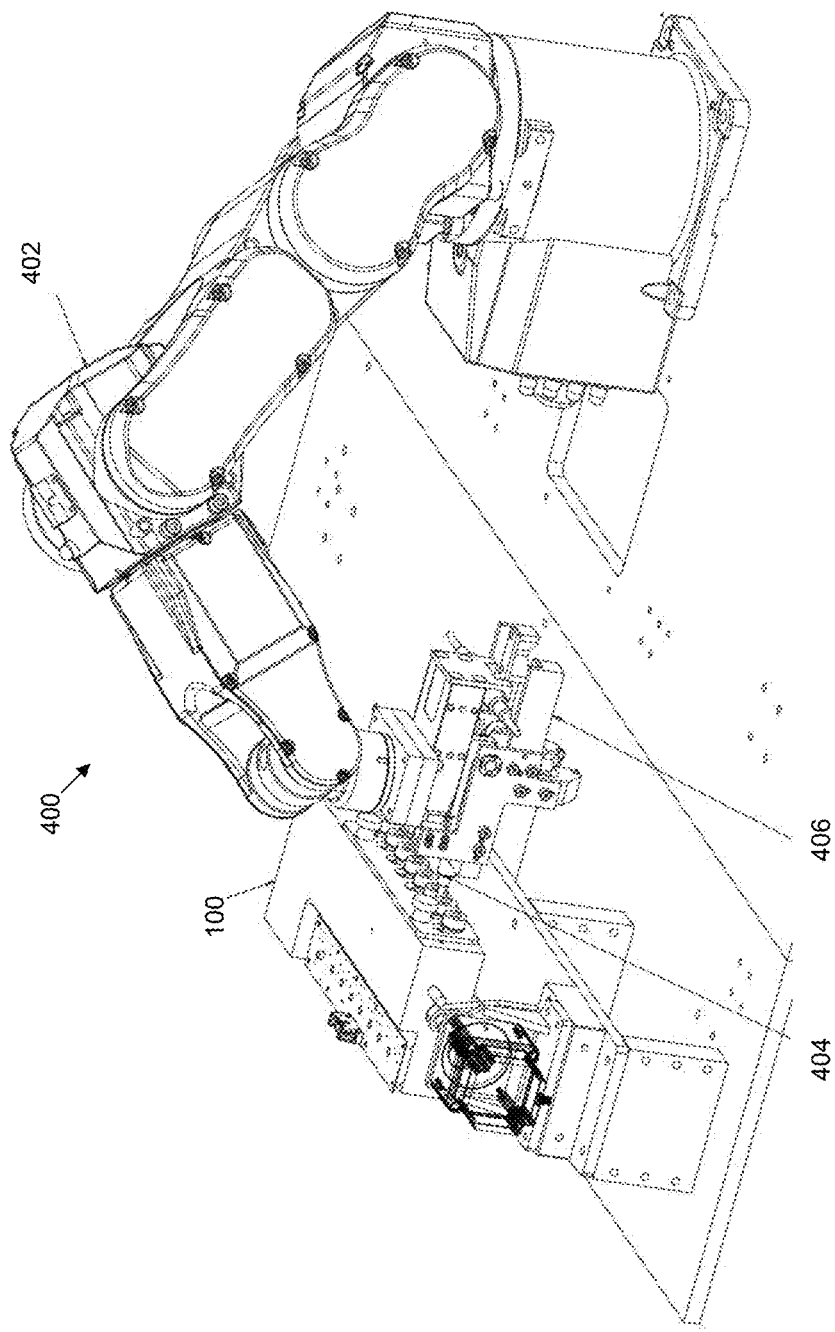
FIG. 4 is a perspective view of a system for determining antimicrobial resistance status of a microorganism from a positive sample bottle, in accordance with an embodiment of the present disclosure.

In FIG. 4, a perspective view of a system 400 for determining antimicrobial resistance status of a microorganism from a positive sample bottle is provided, in accordance with an embodiment of the present disclosure. The system 400 includes the device 100 as described in FIGS. 1-3 as well as a mechanical arm 402 configured to transport the sample from the automated sample culture system to the vial 120.

In some embodiments, the mechanical arm 402 is a robotic arm and operates to access the vials 120, the device 100 for determining antimicrobial resistance status of a microorganism from a positive sample bottle, and possibly other components of an automatic culturing, characterization, and identification system (e.g., a separation and concentration device and/or an identification module). The mechanical arm 402 may also operate to load the sample into the device for determining antimicrobial resistance status. The manner of construction of the mechanical arm 402 can vary widely depending on the configuration of the device 100. In an embodiment, the transfer mechanism may be configured to transfer the positive sample bottles held in the automatic sample culture system (not shown). In this manner, the transfer mechanism may quickly transfer the positive sample bottle from the automatic sample culture system to device 100. Quickly transferring the positive sample bottle reduces the likelihood that the microorganism population will re-enter the lag phase and reduce the time to determination of antimicrobial resistance status.

In some embodiments, the mechanical arm 402 further includes a transfer device 404 for transferring the sample from the positive sample bottle to the vial. In one embodiment, the transfer device 404 is a needle and syringe for withdrawing sample from the positive sample bottle and injecting the sample into the vial (e.g., through the pierceable septum in the cap). As shown in FIG. 4, the housing may be rotatable about a horizontal axis such that the vials can be loaded while horizontal. Given the ability of the housing to rotate and the multiple axes associated with the mechanical arm, the vials can be loaded in a variety of orientations. In some embodiments, the mechanical arm 402 also includes a gripper device 406 for gripping vials 120 and/or positive sample bottles and moving them through the system 400 (e.g., from a disposable vial supply area to the device, etc.).

Figure 5:
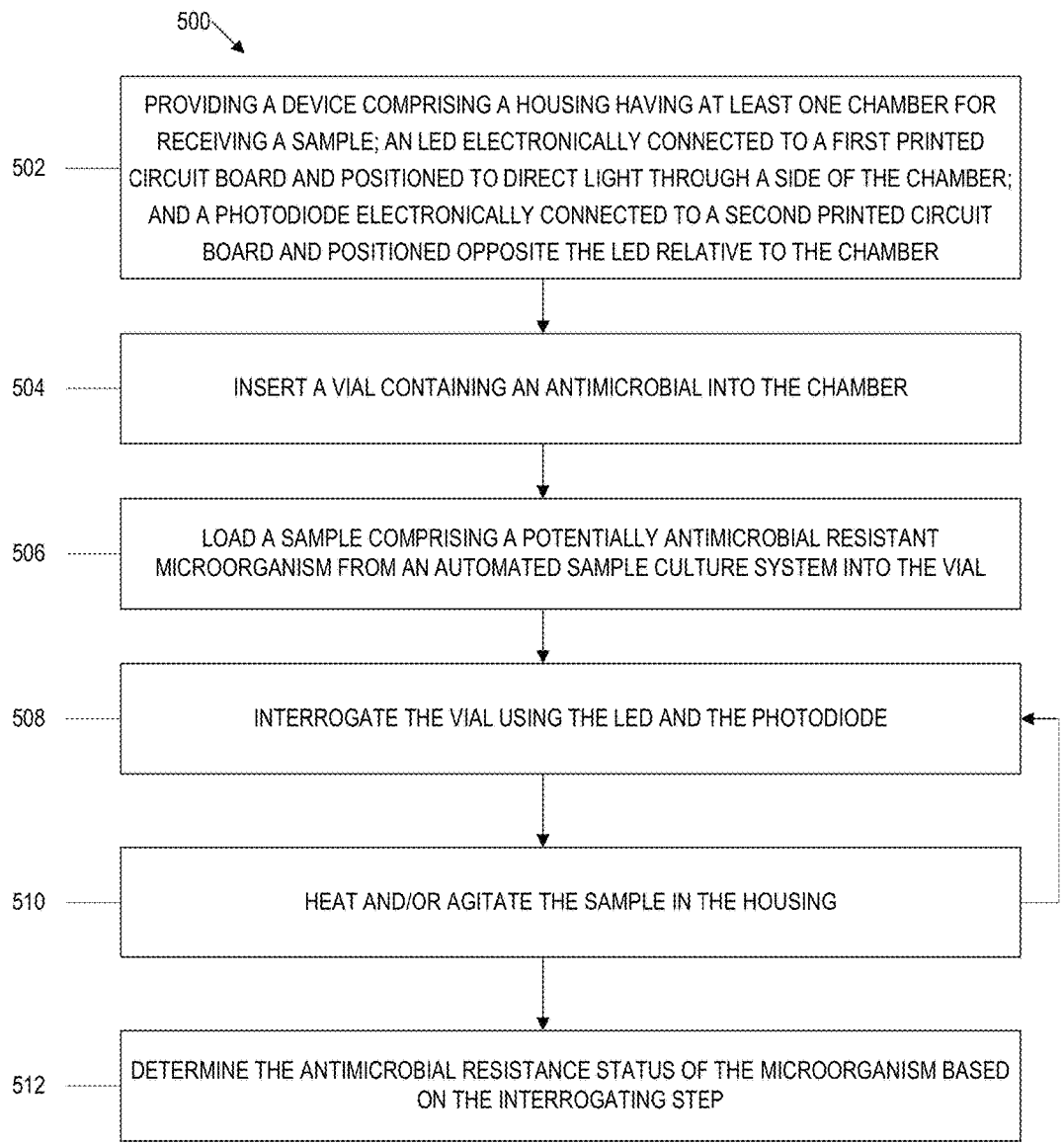
FIG. 5 is a flow chart of a method for determining antimicrobial resistance status of a microorganism from a positive sample bottle, in accordance with an embodiment of the present disclosure.

In another aspect shown in FIG. 5, a method 500 for determining antimicrobial resistance status of a microorganism from a positive sample bottle is provided, in accordance with an embodiment of the present disclosure. In some embodiments, the method 500 includes providing a device comprising a housing having at least one chamber for receiving a sample; a vial containing an antimicrobial in the chamber, a light source positioned to direct light through a side of the chamber; and a photodetector positioned such that light transmitted or scattered by the sample is sensed by the photodetector; placing a sample from an automated sample culture system into the vial; interrogating the vial using the light source and the photodetector; and determining the antimicrobial resistance status of the microorganism in the sample based on the interrogating step. In an embodiment, the method 500 also includes heating and/or agitating the sample in the housing.

As shown in block 502, in one embodiment, the method includes providing an antimicrobial resistance determining device. The device may include any of the features as described in FIGS. 1-4 herein, as well as additional features to implement the steps of the method 500. For example, the device may be as described in FIG. 1 and also include a bar code scanning device (not shown) for identifying the vials loaded into the chambers and a computing device processor for controlling the features of the device.

Turning now to block 504, in some embodiments the method 500 includes inserting a vial containing an antimicrobial into the chamber. In some embodiments, the vial is inserted first and then the antimicrobial is injected at a later point. In one embodiment, the vials are preloaded with antimicrobial solution. In some embodiments, a control vial is also loaded into a second chamber, wherein the control vial does not include antimicrobial solution. The vial may be automatically loaded into the chamber, e.g., via the mechanical arm, or the vial may be manually loaded into the chamber, e.g., via a user.

In some embodiments, the vial is preloaded with a broth before the sample is loaded. For example, pre-warmed cation-adjusted Mueller Hinton broth (CAMBH) or other broth designed to permit or encourage microorganism growth may be preloaded into the vial. In further embodiments, a lysis solution is also included in the vial. In one example, saponin is included in the vial to lyse red blood cells and permit optical density measurements of the microorganisms to be made.

In block 506, the method 500 includes loading a sample comprising a potentially antimicrobial resistant microorganism from an automated sample culture system into the vial. In some embodiments, a predetermined amount of solution from a positive sample bottle is loaded into the vial. For example, in some embodiments, the method also includes a dilution step where warm solution is injected into the vial before or after the sample is loaded to quickly warm the sample and accelerate microorganism growth. For example, the sample may be diluted 1:1, 1:2, 1:4, 1:10, 1:20, 1:40, 1:50, 1:100, or the like in a solution (e.g., broth or media). In one embodiment, the sample is transported to and loaded into the vial using the mechanical arm and transfer device (e.g., needle and syringe). In further embodiments, the positive sample bottle may be warmed in a water bath for a period of time before loading into the vial (e.g., a 36° C. water bath for 15-20 minutes).

In some embodiments, the sample is centrifuged prior to loading into the vial. In this manner, the red blood cells are separated from solution containing lower density microorganisms, and the supernatant may be loaded into the vial. In this embodiment, it is not necessary to add a lytic agent (e.g., saponin) to the vial.

Turning now to block 508, the method 500 includes interrogating the vial using the light source and the photodetector. In some embodiments, an LED emits light at a known wavelength (e.g., 660 nm). The light passes through the vial and some portion of the light is diffracted as a result of the microorganism growth in the vial. The light that passes through the vial is measured by a photodiode over time and the resulting readings are used to determine growth rates and patterns for the microorganism in the vial. The readings may be taken intermittently at varying frequencies, as discussed, or continuously to monitor real-time changes in the optical density of the sample.

In block 510, in some embodiments the method 500 includes heating and/or agitating the sample in the housing. As discussed, the heating device may heat the housing in such a way that the microorganisms in the vials are maintained at a temperature conducive to growth. The heating may maintain the temperature at a set temperature (e.g., 35-37° C.) or may vary the temperature over time (e.g., start at a higher temperature and lower the temperature over time or vice versa). In some embodiments, the heater is configurable to heat different channels to different temperatures.

Similarly, the agitation of the vials encourages growth of the microorganism. The agitation may be intermittent or continuous. In some embodiments, the agitation occurs in random directions. In other embodiments, the agitation is regular. For example, the agitator may rock the housing back and forth along a horizontal axis. By heating and/or agitating the sample, the lag phase of microorganism growth is decreased. Unexpectedly, the lag phase is further decreased when the sample is diluted into pre-warmed media in the vials. As a result, the antimicrobial resistance status of the microorganism can be determined sooner than if the lag phase is extended.

Turning now to block 512, in some embodiments the method 500 includes determining the antimicrobial resistance status of the microorganism based on the interrogating step. As will be explained with reference to Examples A, B, and C herein, in some embodiments determining the antimicrobial status of the microorganism based on the interrogating step comprises comparing the growth curves of the microorganism in the sample in the presence and absence of antimicrobial. A resistant microorganism will display a different growth curve from a wild type or sensitive microorganism. In some embodiments, the resistant microorganism shows an increased growth or a maintenance of population size compared to the wild type. In some embodiments, the sensitive microorganism shows no growth or a decline in population size compared to the resistant microorganism.

In further embodiments, an analysis of the slope of the growth curve of the microorganism population in the vial is used to determine antimicrobial resistance status. For example, the slope of the growth curve may be charted over time determine whether growth is increasing, decreasing, or remaining the same within the vial. In some embodiments, an increase in the slope of a predetermined amount is evidence that growth is occurring in the presence of the antimicrobial agent and the microorganism is therefore determined to be resistant to the concentration of the antimicrobial agent in the vial. In one embodiment, an increase in the slope must be determined for a minimum number of consecutive time points in order for the microorganism to be determined to be antimicrobial resistant. The change in the slope of the growth curve may need to increase a predetermined amount, which could be tailored for the specific microorganism and/or antimicrobial given that different microorganisms may grow a different rates. In some embodiments, a measurement of variation, such as a standard deviation, is used to determine if the slope increased more than would be expected due to random variation in a stable population or due to error in the measurement. Similarly, a microorganism may be determined to be sensitive to the concentration of antimicrobial agent in the vial if the change in the slope of the growth curve over time indicates that the population is not increasing or is decreasing.

EXAMPLES

Example A: Carbapenem-Resistant Enterobacteriaceae (CRE) Assay

BacT/ALERT® SA bottles were inoculated with 10 mL of SPS-anticoagulated normal human blood and seeded with <100 CFU of S. aureus, E. faecalis, E. faecium, E. coli and K. pneumoniae isolates. Within 15 minutes of flagging positive, the bottles were manually unloaded and either tested immediately or kept on ice until tested. If chilled, a positive bottle was warmed in a 36° C. water bath for 15-20 minutes before removing samples. The positive broth dilutions were performed manually.

For the CRE assay, broth containing K. pneumoniae or E. coli isolates was diluted approximately 1:40 into clear, glass tubes containing 9.0 mL of pre-warmed cation-adjusted Mueller Hinton broth (CAMBH) supplemented with 87 μm $ZnSO_4*7H_2O$, 0.05% saponin and ±4 μg/mL imipenem. Saponin lyzed the red blood cells and permitted optical density measurements to be made. Twelve (12) K. pneumoniae and 8 E. coli strains were tested (8 resistant strains containing carbapenemase genes and 12 sensitive strains).

Each strain was sub-cultured without the drug as a growth control. The resistance assay tubes (15 mL tubes fitted with septum screw-caps for diluting and sampling) were incubated in a custom-built, heated, rocking optical density unit, placed within a resistance module, and time-dependent changes in the optical at 660 nm of each culture tube were measured every 45 seconds for periods of up to 12 hours. To maximize microbial growth and minimize measurement noise, tubes were rocked between +/−18 degrees from horizontal at 36 cycles/min for 30 seconds, then returned to the upright position for 15 seconds before an optical density reading was taken.

For the rapid detection of carbapenem-resistant Enterobacteriaceae in positive blood cultures, 20 broth samples known to contain potentially resistant species were diluted with and without 4 μg/mL of imipenem, and the culture optical density continuously monitored for up to 12 hours (8 resistant and 12 sensitive strains).

Figure 6A:
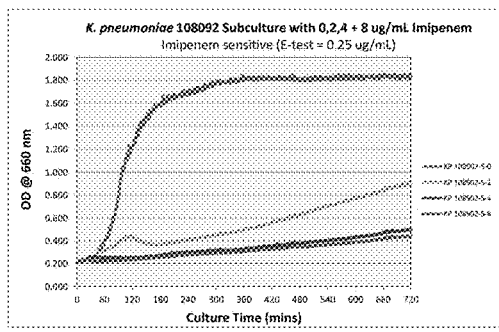
FIGS. 6A, 6B, 6C, and 6D are graphs of optical density vs. culture time to identify carbapenem-resistant Enterobacteriaceae, in accordance with an embodiment of the present disclosure.
Figure 6C:
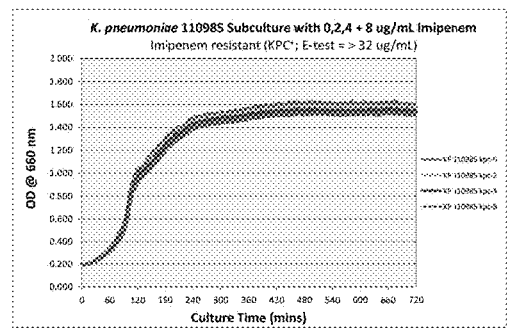
Figure 6B:
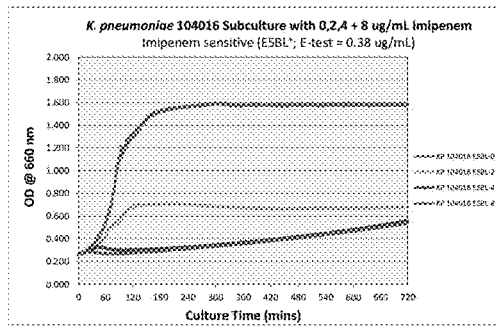
Figure 6D:
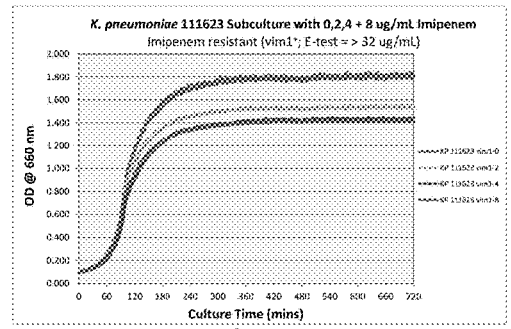

Examples of a preliminary imipenem titration on 4 K. pneumoniae strains is shown in FIGS. 6A, 6B, 6C, and 6D. FIG. 6A provides optical density results of the interrogation over time on a sensitive strain of K. pneumoniae. As can be seen in FIG. 6A, the sensitive K. pneumonia cultured without antimicrobial (KP 108902-S-0) had a normal growth phase as measured by optical density over time. In contrast, as the concentration of antimicrobial increased from 2 μg/ml to 4 μg/ml and 8 μg/ml, the growth curves of the sensitive K. pneumonia indicated a decrease in microorganism growth. FIG. 6B provides optical density results of the interrogation over time on a carbapenem-sensitive strain producing extended spectrum beta-lactamases (ESBLs). Again, the culture having no antimicrobial exhibited a normal growth curve but the cultures having increasing concentrations of antimicrobial exhibited decreased growth. FIG. 6C provides optical density results of the interrogation over time on a carbapenem-resistant strain (kpc). Here, the growth curves of the resistant K. pneumonia were not dependent upon the concentration of antimicrobial present in the culture. Similarly, FIG. 6D provides optical density results of the interrogation over time on a different resistant strain (vim 1). Again, the growth curves of the resistant K. pneumonia were not dependent upon the concentration of antimicrobial present in the culture. As a result of these findings, a concentration of 4 μg/mL (red curve) was chosen as the breakpoint for testing additional strains in this direct-from-blood culture assay.

All 8 strains harboring carbapenemase genes (six *K. pneumoniae* [5 kpc and 1 vim1] and two *E. coli* [imp4 and vim1]) grew vigorously in the presence of 4 ug/mL imipenem within 2 hours, whereas none of the 12 imipenem sensitive strains, including 6 producing ESBLs, grew over the 12-hr culture period. The results of Example A indicate that optical density over time can be used to monitor growth rates of microorganisms in the presence and absence of antimicrobials.

Example B: Methicillin-Resistant *Staphylococcus aureus* (MRSA) Assay

The BacT/ALERT® SA bottles were inoculated as described in Example A. The positive broth dilution for the MRSA Assay was performed as follows: broth containing a *S. aureus* isolate was diluted 1:20 into glass tubes containing 9.0 mL of pre-warmed CAMBH, 0.05% saponin and ±6 μg/mL cefoxitin. Ten (10) *S. aureus* strains representing diverse phenotypes were tested (5 resistant and 5 sensitive).

Each strain was sub-cultured without the drug as a growth control. The resistance assay tubes (15 mL tubes fitted with septum screw-caps for diluting and sampling) were incubated in a custom-built, heated, rocking optical density unit, placed within a resistance module, and time-dependent changes in the optical at 660 nm of each culture tube were measured every 45 seconds for periods of up to 12 hours. To maximize microbial growth and minimize measurement noise, tubes were rocked between +/−18 degrees from horizontal at 36 cycles/min for 30 seconds, then returned to the upright position for 15 seconds before an optical density reading was taken.

To detect MRSA directly from positive blood cultures, 10 broth samples containing *S. aureus* strains representing diverse phenotypes were sub-cultured for up to 12 hours with and without 6 μg/mL of cefoxitin (5 resistant and 5 sensitive strains).

Figure 7A:
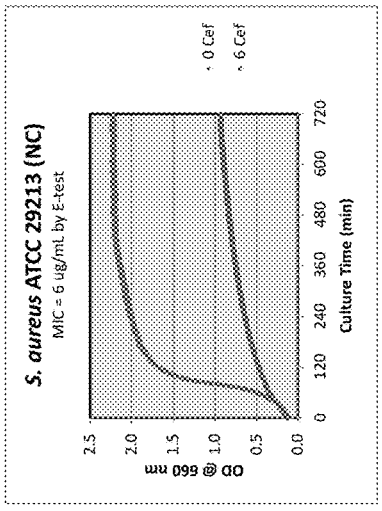
FIGS. 7A, 7B, 7C, 7D, 7E, and 7F are graphs of optical density vs. culture time to identify methicillin-resistant Staphylococcus aureas, in accordance with an embodiment of the present disclosure.

The optical density growth curves correlated 100% with the known oxacillin resistance category of all 10 strains. All 5 sensitive strains failed to grow by 12 hours (example red curves in FIGS. 7A and 7B). Three (3) of the 5 MRSA strains demonstrated growth in the cefoxitin media within 2 hours, the Positive Control strain ATCC 43300 by 2.5 hours (FIGS. 7C and 7D), and the last, weakly resistant strain (E-test MIC=16 ug/mL) was detected by 4.5 hours (FIGS. 7E and 7F).

Figure 7B:
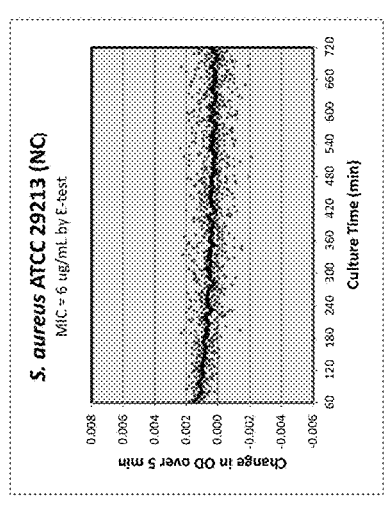
Figure 7C:
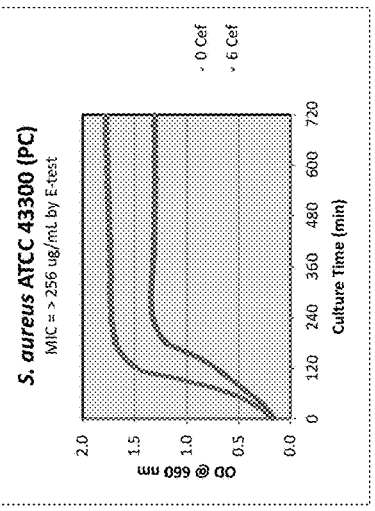
Figure 7D:
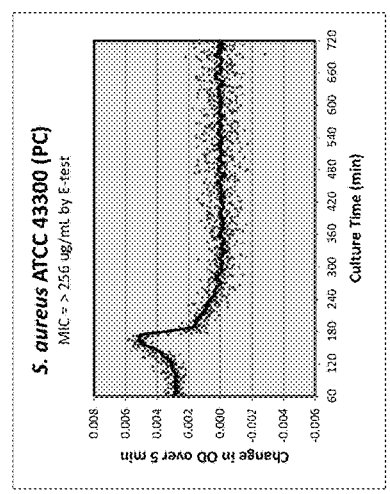
Figure 7E:
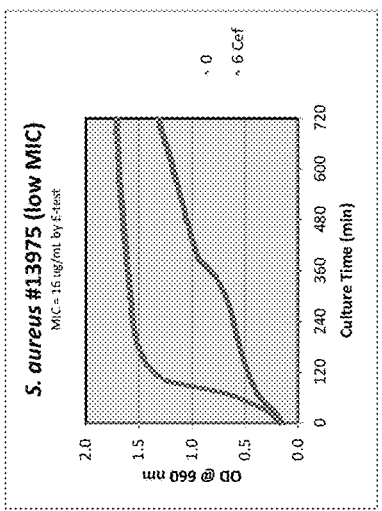
Figure 7F:
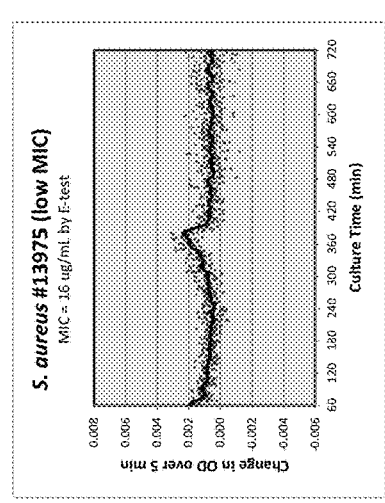

To better discriminate microbial growth from background increases in media optical density, slopes of the growth curves were calculated and plotted (FIGS. 7B, 7D, and 7F). Following a 60 min equilibration period, all 5 sensitive strains had decreasing or flat slopes over 720 min (see example in FIG. 7B).

Example C: Vancomycin-Resistant Enterococci (VRE) Assay

The BacT/ALERT® SA bottles were inoculated as described in Example A. The positive broth dilution for the MRSA Assay was performed as follows: broth containing *E. faecium* or *E. faecalis* isolates was spun for 10 seconds @10,600 g in a 1.5 mL microcentrifuge tube to sediment red blood cells (RBC). One (1.0) mL of the RBC depleted supernatant was recovered and diluted into 4.0 mL of pre-warmed BacT/ALERT® SA media±6 μg/mL vancomycin. Thirty-one (31) *E. faecium* and 7 *E. faecalis* strains were tested (23 resistant and 15 sensitive).

To rapidly detect VRE in positive blood cultures, 38 broth samples containing *E. faecium* and *E. faecalis* strains were depleted of red blood cells and then diluted 1:5 in BacT/ALERT® SA blood culture media with and without 6 μg/mL of vancomycin (23 resistant and 15 sensitive strains).

Figure 8A:
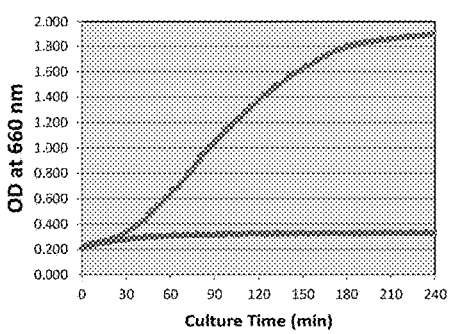
FIGS. 8A, 8B, 8C, and 8D are graphs of optical density vs. culture time to identify vancomycin-resistant enterococci, in accordance with an embodiment of the present disclosure.
Figure 8C:
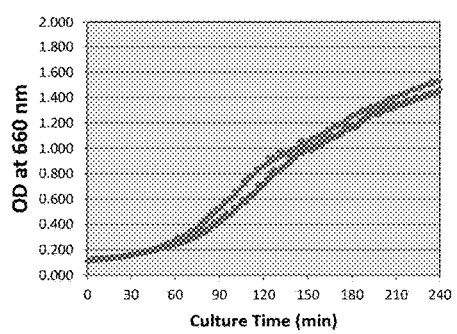
Figure 8B:
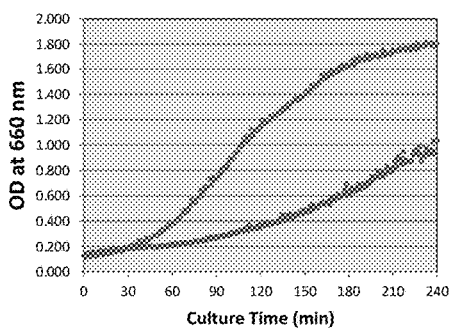
Figure 8D:
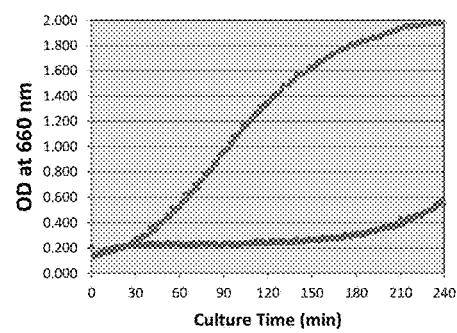

100% of the strains were correctly called as VRE or VSE (sensitive) within the following 4 hours (FIGS. 8A-8D). FIG. 8A discloses optical density as a function of time of a sensitive strain in the presence (red line) and absence (blue line) of vancomycin. All 17 resistant *E. faecium* strains were detected within 2 hours (FIGS. 8B and 8C), while three low MIC (16-64 ug/mL), van B containing *E. faecalis* strains were not detected until after 3-4 hours of culture with vancomycin (example strain given in FIG. 8D). The CLSI Positive Control strain ATCC 51299 (MIC=16-24) is a good example of this last group. This strain is an example of the antimicrobial resistance mechanism of induced resistance, where the population of resistant cells are initially inhibited by the antimicrobial agent until the genes or set of genes responsible for resistance can be up-regulated (e.g., by the antibiotic) and the resistant cells then begin to grow. Unexpectedly, a higher cell concentration was found to be beneficial for faster detection of these delayed van B isolates. Increasing the starting subculture optical density from <0.10 to the 0.25-0.45 range resulted in detection by 2-2.5 hours (data not shown). Using this growth-based VRE assay, it was determined that the microbial cell concentration in the positive blood culture plays a significant role in generating a faster result.

These laboratory studies demonstrate the feasibility of using automated subculture immediately post-detection and a heated, rocking optical density reader to predict the resistance of an isolate to several widely-used antimicrobials directly from positive blood culture bottles within 5 hours of detection. Faster results (≤2 hours) were obtained with CRE and vancomycin-resistant *E. faecium* strains. While the broth dilution steps were performed manually in this study, the assays can be fully automated by incorporating the optical density reader into a robotic blood culture processor.

The present invention is described in part with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The flowcharts and block diagrams of certain of the figures herein illustrate exemplary architecture, functionality, and operation of possible implementations of embodiments of the present invention. It should be noted that in some alternative implementations, the steps noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

We claim:

1. A device for determining the antimicrobial resistance status of a microorganism from a sample bottle in which a microbial culture has grown, the device comprising:
   (a) a housing having at least one chamber for receiving a sample;
   (b) an agitation device operably connected to the housing and configured to agitate the housing, wherein the agitation device is a step motor configured to rock the housing at least +/−18° from horizontal:
   (c) a light source positioned to direct light through a side of the chamber; and
   (d) a photodetector positioned such that light transmitted or scattered by the sample is sensed by the photodetector.

2. The device of claim 1, wherein the light source is an LED electronically connected to a first printed circuit board.

3. The device of claim 1, wherein the photodetector is a photodiode electronically connected to a second printed circuit board.

4. The device of claim 1, wherein the photodetector is positioned at an angle from the light source selected from the group consisting of 90° and 180°.

5. The device of claim 1, further comprising a heat source thermally connected to the housing.

6. The device of claim 5, wherein the heat source is configured to maintain a temperature of the chamber at between about 20° C. and about 45° C.

7. The device of claim 1, wherein the agitation device continuously agitates the housing as the photodetector senses light to generate real-time measurements of optical density of the sample.

8. The device of claim 1, further comprising a vial containing an antimicrobial.

9. The device of claim 8, further comprising a mechanical arm configured to transport the sample from an automated sample culture system to the vial.

10. A device for determining the antimicrobial resistance status of a microorganism from a sample bottle in which a microbial culture has grown, the device comprising:
    (a) housing having at least one chamber for receiving a sample;
    (b) an LED electronically connected to a first printed circuit board and positioned to direct light through a side of the chamber;
    (c) a photodiode electronically connected to a second printed circuit board and positioned such that light transmitted or scattered by the sample is sensed by the photodiode;
    (d) a rubber heater adhered to the side of the housing and configured to maintain a temperature of the at least one chamber at between about 20° C. and about 45° C.; and
    (e) a step motor configured to rock the housing at least +/−18° from horizontal.

11. A method for determining the antimicrobial resistance status of a microorganism from a sample bottle in which a microbial culture has grown, the method comprising:
    (a) providing a device comprising:
        (i) a housing having at least one chamber for receiving a sample;
        (ii) a vial containing an antimicrobial in the chamber;
        (iii) an agitation device operably connected to the housing and configured to agitate the housing, wherein the agitation device is a step motor configured to rock the housing at least +/−18° from horizontal;
        (iv) a light source positioned to direct light through a side of the chamber; and
        (v) a photodetector positioned such that light transmitted or scattered by the sample is sensed by the photodetector;
    (b) loading a sample from an automated sample culture system into the vial;
    (c) interrogating the vial using the light source and the photodetector during a culture period; and
    d) determining the antimicrobial resistance status of the microorganism in the sample based on the interrogating step, wherein the microorganism is determined to be resistant to the antimicrobial if there is growth in the vial.

12. The method of claim 11, wherein the light source is an LED electronically connected to a first printed circuit board.

13. The method of claim 11, wherein the photodetector is a photodiode electronically connected to a second printed circuit board.

14. The method of claim 11, further comprising heating the sample bottle in the chamber.

15. The method of claim 14, wherein the heating maintains the sample bottle at between about 20° C. and about 45° C.

16. The method of claim 11, further comprising agitating the housing using a step motor.

17. The method of claim 16, wherein the agitating rocks the housing at least +/−18° from horizontal.

18. The method of claim 16, further comprising continuously agitating the housing while interrogating the vial to generate real-time measurements of optical density of the sample.

19. The method of claim 11, further comprising transporting the sample from the automated sample culture system to the vial using a mechanical arm.

20. The method of claim 11, further comprising determining a change in an optical density of the sample over time.

21. The method of claim 20, wherein the device further comprises a control vial having no antimicrobial, and wherein the method further comprises:
    a) placing a control sample from the automated sample culture system into the control vial, wherein the sample and the control sample are from the sample bottle;
    b) interrogating the control vial using the LED and the photodiode;
    c) determining a change in an optical density of the control sample over time; and
    d) comparing the change in the optical density of the sample over time to the change in the optical density of the control sample over time, wherein the growth of the control sample over time represents growth that is not affected by the antimicrobial.

22. The method of claim 20, further comprising determining a growth curve for the microorganism based on the change in the optical density of the sample over time.

23. The method of claim 11, further comprising determining that the microorganism is resistant to the antimicrobial based on an analysis of a slope of a growth curve for the microorganism at any time during the culture period.

24. The method of claim 23, wherein the analysis determines that the slope of the growth curve increased at least a predetermined amount at any time during the culture period.

25. The method of claim 11, further comprising determining that the microorganism is sensitive to the antimicrobial when a slope of a growth curve for the microorganism is decreasing or flat throughout the culture period.

26. The method of claim 11, further comprising determining that the microorganism is sensitive to the antimicrobial when a slope of a growth curve for the microorganism is less than a predetermined amount.

* * * * *